US012766050B2

(12) United States Patent
Sun et al.

(10) Patent No.: US 12,766,050 B2
(45) Date of Patent: Oct. 20, 2026

(54) HYDROPHILIC NONWOVEN HAVING APERTURES AND ABSORBENT ARTICLE COMPRISNG THE SAME

(71) Applicant: The Procter & Gamble Company, Cincinnati, OH (US)

(72) Inventors: Xiaojuan Sun, Beijing (CN); Gueltekin Erdem, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 483 days.

(21) Appl. No.: 18/476,376

(22) Filed: Sep. 28, 2023

(65) Prior Publication Data

US 2024/0115433 A1 Apr. 11, 2024

(30) Foreign Application Priority Data

Sep. 30, 2022 (WO) ................ PCT/CN2022/123024

(51) Int. Cl.
*A61F 13/15* (2006.01)
*A61F 13/512* (2006.01)

(52) U.S. Cl.
CPC .... *A61F 13/5123* (2013.01); *A61F 13/15707* (2013.01)

(58) Field of Classification Search
CPC ................ A61F 13/512; A61F 13/5123; A61F 13/15577; A61F 13/15699; A61F 13/15707
USPC ................................ 604/379, 380, 383, 382
See application file for complete search history.

(56) References Cited

U.S. PATENT DOCUMENTS

| | | | |
|---|---|---|---|
| 11,369,527 B2 | 6/2022 | Rosati et al. | |
| 2014/0121625 A1* | 5/2014 | Kirby ................ | A61F 13/51108 604/383 |
| 2018/0071156 A1 | 3/2018 | Rosati et al. | |
| 2019/0117472 A1* | 4/2019 | Erdem ...................... | B32B 7/14 |

OTHER PUBLICATIONS

PCT Search Report and Written Opinion for PCT/CN2022/123024 dated Mar. 9, 2023, 10 pages.
Extended EP Search Report and Opinion for Application No. 23199306.4; dated Jan. 26, 2024, 07 pages.

* cited by examiner

*Primary Examiner* — Jacqueline F Stephens
(74) *Attorney, Agent, or Firm* — Daniel S. Albrecht

(57) ABSTRACT

The present disclosure is related to a nonwoven comprising a first layer free from cellulose-based fibers. The first layer comprises a first surface, an opposite second surface, and a plurality of apertures. The first surface of the first layer comprises a hydrophilic non-aperture area having a first non-aperture area contact angle as measured by a Contact Angle Test. Each of a majority of the plurality of apertures has a side wall having an aperture contact angle as measured by the Contact Angle Test. The aperture contact angle is higher than the first non-aperture area contact angle.

18 Claims, 11 Drawing Sheets

HYDROPHILIC NONWOVEN HAVING APERTURES AND ABSORBENT ARTICLE COMPRISNG THE SAME

CROSS REFERENCE TO RELATED APPLICATION

This application claims priority, under 35 U.S.C. § 119, to PCT Patent Application PCT/CN2022/123024, filed on Sep. 30, 2022, the entire disclosure of which is hereby incorporated by reference.

FIELD

The present invention relates to an apertured nonwoven and an absorbent article comprising the same.

BACKGROUND

Absorbent articles have been used as personal hygiene products, such as sanitary napkins, infant disposable diapers, training pants for toddlers, adult incontinence undergarments, and the like. Such absorbent articles are designed to absorb and contain body exudates, in particularly large quantities of urine, runny BM, and/or menses (together the “fluids”). These absorbent articles may comprise several layers providing different functions, for example, a topsheet, a backsheet, and an absorbent core disposed therebetween, among other layers (e.g., acquisition layer, distribution layer, etc.) as desired.

One of design criteria of topsheets in absorbent articles is to reduce the amount of time the fluids spend on the topsheet prior to being absorbed by the absorbent article. If the fluids remain on the surfaces of the topsheets for too long of a period of time, wearers may feel unpleasant wetness, and discomfort may increase. Another desirable quality of topsheets is prevention of fluid flow-back through a topsheet and provision of dryness feel.

Hydrophobic topsheets have long stay of the fluid on the topsheets before the fluid is able to be absorbed by the absorbent article. To solve problems due to prolonged fluid residency on topsheets such as run-off and fluid leakage, apertured topsheets have been used to aim at faster fluid penetration into the absorbent article. Although apertured topsheets generally reduce fluid pendency on topsheets by enabling faster body fluids penetration, apertured hydrophobic topsheets may nevertheless still have slow acquisition speed compared to hydrophilic topsheets, and a relatively high run-off due to relatively small apertures through which liquid only slowly or even not at all penetrates the topsheets. Increase of aperture size may cause fluid flow-back through the big size apertures.

Absorbent articles with hydrophilic topsheets are known to exhibit faster fluid acquisition speed compared to ones with hydrophobic topsheets, however, tend to hold the fluid among hydrophilic fibers which tend to cause fluid flow-back through topsheets, and uncomfortable wet feeling to the wearers.

In general, apertures in topsheets are desired as they can communicate functional perceptions such as high breathability and fast fluid acquisition, but tend to increase rewet as fluid may come back from layers underneath the topsheet through apertures, and fluid retained in apertures and small pores in the periphery of apertures touches the skin.

This is also important that we enable apertures that helps speed & perception benefit while it does not hurt rewet.

There is still a need for a nonwoven provides reduced rewet without compromising fluid acquisition speed when it is used in absorbent articles.

There is still a need for an absorbent article with a topsheet provides reduced rewet onto the wearer-facing surface of the absorbent article without compromising fluid acquisition speed.

SUMMARY

The present invention relates to a nonwoven which comprises a first layer free from cellulose-based fibers, the first layer comprising a first surface, an opposite second surface, and a plurality of apertures. The first surface of the first layer comprises a hydrophilic non-aperture area having a first non-aperture area contact angle as measured by Contact Angle Test. Each of majority of the apertures has a side wall having an aperture contact angle as measured by Contact Angle Test which is higher than the first non-aperture area contact angle.

The present invention also relates to an absorbent article comprising: a topsheet, a backsheet, and an absorbent core disposed between the topsheet and the backsheet, wherein the topsheet comprises the nonwoven according to the present invention, and wherein the first surface of the first layer forms at least part of a wearer facing surface of the absorbent article. The present invention also relates to a method for producing an apertured nonwoven comprising steps of:

a) providing a first layer free from cellulose-based fibers, a first surface and an opposite second surface,
b) providing an aperturing apparatus comprising a first forming member and a second forming member which engages the first forming member, wherein the first forming member comprises a plurality of pins on its surface and the second forming member comprises a plurality of recesses on its surface,
c) wetting the pins on the first forming member with a treatment having a HLB value not higher than about 13, and
d) moving the first layer between the first and second forming members so that apertures are formed in the first layer as the pins on the first forming member and the recesses on the second forming member are engaged, wherein the first surface of the first layer comprises a land area having a first non-aperture area contact angle measured by Contact Angle Test, and wherein each of majority of the apertures has a side wall having an aperture contact angle as measured by Contact Angle Test, the aperture contact angle being higher than the non-aperture area contact angle.

For ease of discussion, the absorbent article will be discussed with reference to the numerals referred to in these figures. The figures and detailed description should however not be considered limiting the scope of the claims, unless explicitly indicated otherwise, and the invention disclosed herein is also used in a wide variety of absorbent article forms.

DETAILED DESCRIPTION

Figure 1A:
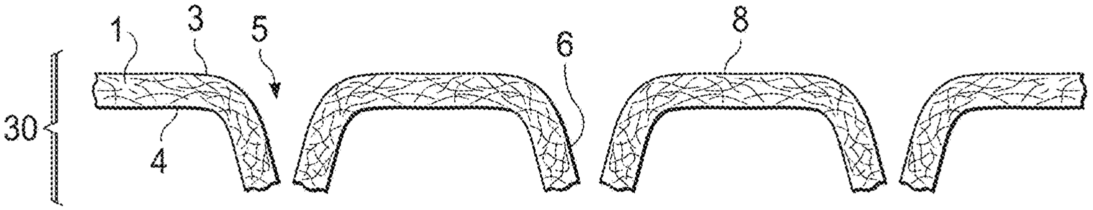
FIG. 1A is a schematic view of a nonwoven having a first layer in accordance with the present invention.

Various non-limiting forms of the present disclosure will now be described to provide an overall understanding of the principles of the structure, function, manufacture, and use of an absorbent article comprising an apertured topsheet free from cellulose-based fibers having mitigated rewet and fast fluid acquisition speed. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments, feminine hygiene products such as sanitary napkins, menstrual pants, and pantyliners, and wipes.

As used herein, the term "cellulose-based fibers" intends to include both natural cellulose fibers such as pulp and cotton, and regenerated cellulose fibers such as rayon (including viscose, lyocell, MODAL (a product of Lenzing AG, Lenzing, Austria) and cuprammonium rayon) unless specified differently.

As used herein, the terms "hydrophilic" and "hydrophobic" have meanings that are well established in the art with respect to the contact angle of water on the surface of a material. Thus, a material or a fiber having a water contact angle of greater than about 90° as measured by Contact Angle Test is considered hydrophobic, and a material or a fiber having a water contact angle of less than about 90° as measured by Contact Angle Test is considered hydrophilic.

As used herein, the term "natural fibers" refers to elongated substances produced by plants and animals and comprises animal-based fibers and plant-based fibers. Natural fibers may comprise fibers harvested without any post-harvest treatment step as well as those having a post-treatment step, such as, for example, washing, scouring, and bleaching.

As used herein, the term "plant-based fibers" comprises both harvested fibers and synthetic fibers that comprise bio-based content. Harvested plant-based fibers may comprise cellulosic matter, such as wood pulp; seed hairs, such as cotton; stem (or bast) fibers, such as flax and hemp; leaf fibers, such as sisal; and husk fibers, such as coconut.

Nonwoven

The nonwoven of the present invention comprises synthetic fibers such as thermoplastic fibers, and is free from cellulose-based fibers.

The nonwoven of the present the invention comprises a first layer comprising thermoplastic fibers. The nonwoven of the present the invention may further comprise a second layer comprising thermoplastic fibers. The nonwoven may be formed of a single layer, of two layers, or, of more than two layers.

Synthetic fibers may be selected from the group consisting of polyesters, polypropylenes, polyethylenes, polyethers, polyamides, polyhydroxyalkanoates, polysaccharides, and combinations thereof. Additionally, other synthetic fibers such as rayon, polyethylene, and polypropylene fibers can be used within the scope of the present disclosure.

Thermoplastic fibers may be single component fibers (i.e., single synthetic material or a mixture to make up the entire fiber), multicomponent fibers, such as bicomponent fibers (i.e., the fiber is divided into regions, the regions including two or more different synthetic materials or mixtures thereof), or combinations thereof.

The nonwoven may also comprise semi-synthetic fibers made from polymers, specifically hydroxyl polymers. Non-limiting examples of suitable hydroxyl polymers include polyvinyl alcohol, starch, starch derivatives, chitosan, chitosan derivatives, and combinations thereof.

Several examples of nonwoven may include but are not limited to: spunbonded nonwovens; carded nonwovens; carded air through nonwovens; spunlace nonwovens, needle punched nonwovens and nonwovens with relatively specific properties to be able to be readily deformed. The nonwoven can be formed from many processes, such as, for example, air laying processes, wetlaid processes, meltblowing processes, spunbonding processes, needle punching processes and carding processes. The fibers in the nonwoven can then be bonded via spunlacing processes, hydroentangling, calendar bonding, through-air bonding and resin bonding.

The nonwoven may have a basis weight from about 10 to about 200 g/m$^2$, or from about 20 to about 100 g/m$^2$, or about 25 to about 60 g/m$^2$, or about 30 to about 50 g/m$^2$.

First Layer

The first layer comprises thermoplastic fibers. The list of thermoplastic fibers and the nonwoven web manufacturing process correspond to the list and process disclosed above for the nonwoven.

The first layer comprises a first surface, an opposite second surface and a plurality of apertures. The first surface of the first layer comprises at least one non-aperture area which has no aperture.

The non-aperture area may fully surround the apertures. The non-aperture area may together form a generally continuous grid throughout the first surface of the first layer, while the apertures may be discrete elements dispersed in and surrounded by the continuous grid.

The non-aperture area may be a plurality of discrete areas defined by apertures. Each of the plurality of discrete non-aperture areas has a periphery formed by a continuous line of apertures, with adjacent apertures being spaced apart by an edge-to-edge distance of no more than 3 mm. Further, each of the plurality of discrete non-aperture areas is substantially free of apertures within the periphery.

The non-aperture area may be a land area and/or a protrusion.

The non-aperture area is hydrophilic and has a first non-aperture area contact angle. The first non-aperture area contact angle may be no greater than about 80°, or no greater than about 70°, or no greater than about 50°, as measured by Contact Angle Test. The non-aperture area may comprise hydrophilic fibers, or fibers treated with a hydrophilic treatment.

Hydrophobic fibers may be rendered hydrophilic by treatment with a hydrophilic treatment such as a hydrophilic surfactant, e.g., by spraying or kiss roll coating hydrophobic thermoplastic fibers with a hydrophilic treatment, by dipping the fiber into a treatment or by including a hydrophilic treatment as part of the polymer melt in producing thermoplastic fibers. Upon melting and resolidification, the treatment will tend to remain at the surfaces of the fiber.

The non-aperture area of the first surface may be free of a treatment. The non-aperture area of the first surface may comprise a hydrophilic treatment.

The first layer comprises a plurality of apertures. Each of majority of the plurality of apertures comprises a side wall having an aperture contact angle as measured by Contact Angle Test, the aperture contact angle being higher than the first non-aperture area contact angle. The aperture contact angel may be equal to or higher than about 85°, or equal to or higher than about 90°, or equal to or higher than about 100°, as measured by Contact Angle Test. The aperture contact angle may be higher than the first non-aperture area contact angle by at least 10°, or by at least 15°, or by at least 20°.

The side wall of each aperture may be treated with a treatment such as a hydrophobic treatment. The treatment may have a HLB value not higher than about 13.

The HLB values for commonly-used treatments are readily available in the literature (e.g., HLB Index in *McCutcheon's Emulsifiers and Detergents*, MC Publishing Co., 2004). Another way of obtaining HLB values is to estimate by calculations. The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20. Other examples of how to calculate HLB values are described by Davies in *Interfacial Phenomena,* 2nd Edition, Academic Press, London, 1963 and by Lin in *J. Phys. Chem.* 76, 2019-2013, 1972.

The first layer may comprise a mixture of hydrophobic fibers and hydrophilic fibers. The amount of hydrophilic fibers may be higher than the amount of hydrophobic fibers. For example, the first layer may comprise a mixture of from 5% to 40% by weight of hydrophobic fibers and from 60% to 95% by weight of hydrophilic fibers by total weight of the first layer. For example, the first layer may comprise a mixture of from 5% to 40% by weight of hydrophobic synthetic fibers and from 60% to 95% by weight of hydrophilic fibers by total weight of the first layer. The first layer may comprises 100% hydrophilic fibers.

The first layer may be a carded nonwoven layer.

The first layer may have various structures.

Referring to FIG. 1A, nonwoven 30 of the present invention comprises at least a first layer 1. The first layer 1 comprises a first surface 3 and a second surface 4.

The first layer 1 comprises a plurality of apertures 5. To ensure material stability, the smallest edge-to-edge distance between the majority of the apertures regardless of their particular shape and width may be at least 0.5 mm, or at least 1.5 mm or 2.0 mm. This distance is measured on the first surface 3 of the first layer 1 of the topsheet.

The apertures may vary in shape. For example, the shape of the apertures as seen from the first surface of the first layer may be circular, elliptic, rectangular or polygonal. In one embodiment, the apertures have a circular shape, an elliptic shape or a polygonal shape.

The tridimensional shape of the apertures may be cylindrical (e.g. with a circular or elliptic base), prismatic (e.g. with a polygonal base) or truncated cone or pyramidal.

Each of the apertures 5 has a side wall 6. The side wall 6 may extend outwardly, away from land area 8 of the second surface of the first layer, as shown in FIG. 1A. When the nonwoven described herein is incorporated into an absorbent article, the direction of the side walls of the apertures, when extending outwardly, may be towards the absorbent core of the absorbent article.

The amount of extension of the side walls of the apertures may be at least 0.1 mm beyond the second surface of the first layer, or at least 0.2 mm beyond the second surface of the first layer. The side walls of the apertures may form funnels or channels.

Figure 1B:
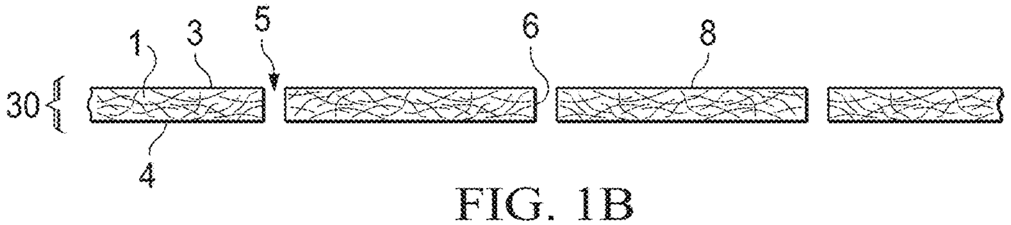
FIG. 1B is a schematic view of a nonwoven having a first layer in accordance with the present invention.

The side wall 6 may not extend outwardly as shown in FIG. 1B.

The apertures may be tapered and take a conical shape such that the diameter of the aperture is larger at a part of the aperture proximate to the first surface of the first layer than the diameter of the aperture at the bottom edge of the aperture.

Such tapered configuration helps to reduce the risk of rewet, i.e. of body liquids passing back from components underneath the topsheet (such as the absorbent core) into and through the topsheet. With apertured topsheets, rewet may be caused by fluid-back through the apertures. The tapered shape of the apertures can help to reduce rewet, as the diameter of the aperture towards the absorbent core is smaller than the diameter of the aperture in the first layer.

The plurality of apertures may also vary in width.

The majority of the apertures may comprise a treatment.

The treatment may be applied via pin coating described in detail later or other application processes known in the art. The treatment can be applied to the majority of the apertures via aperturing forming process such as the pin aperturing processes, or via printing processes.

The apertures of the first layer of the topsheet may have at least about 2.5% of an open area, or at least about 3% of an open area for the fast fluid acquisition speed purposes. The apertures of the first layer of the topsheet may have an open area no greater than about 30%, no greater than about 28%, or no greater than about 25% of open area for mitigating or preventing rewet purposes.

Each of majority of the apertures, or at least 70% of the apertures, or at least 80% of the apertures, or at least 90% of the apertures has a side wall having an aperture contact angle as measured by Contact Angle Test, the aperture contact angle being higher than the first non-aperture area contact angle.

The size of apertures may be determined to achieve the desired fluid and/or air penetration performance and other performances expected by wearers. If the apertures are too small, the fluids may not pass through the apertures, either due to poor alignment of the fluid source and the aperture location or due to runny fecal masses, for example, having a diameter greater than the apertures. If the apertures are too large, the area of skin that may be contaminated by "rewet" from the article is increased.

When the majority of the apertures have side walls having an aperture contact angles higher than the first non-aperture area contact angle, each of the plurality of apertures may have a size ranging from 0.2 $mm^2$ to 1.5 $mm^2$, from 0.2 $mm^2$ to 1.0 $mm^2$, or from 0.25 $mm^2$ to 0.5 $mm^2$, and/or a diameter ranging from 0.3 mm to 1.5 mm, or from 0.3 mm to 1 mm, or from 0.4 mm to 0.8 mm. The plurality of apertures may have regular shapes selected from the group consisting of circle, oval, triangle, square, rectangle, parallelogram, trapezoid, polygon, hourglass, star, and any combinations thereof.

Apertures in the nonwoven or the topsheet in the present invention are less likely to trap or retain fluid by fibers or in between fibers thanks to sidewalls having an aperture contact angle higher than the first non-aperture area contact angle as measured by Contact Angle Test. Therefore, nonwoven disclosed herein provides improved fluid handling properties such as a reduced rewet onto the wearer-facing surface of the absorbent article without compromising fluid acquisition speed.

Figure 2:
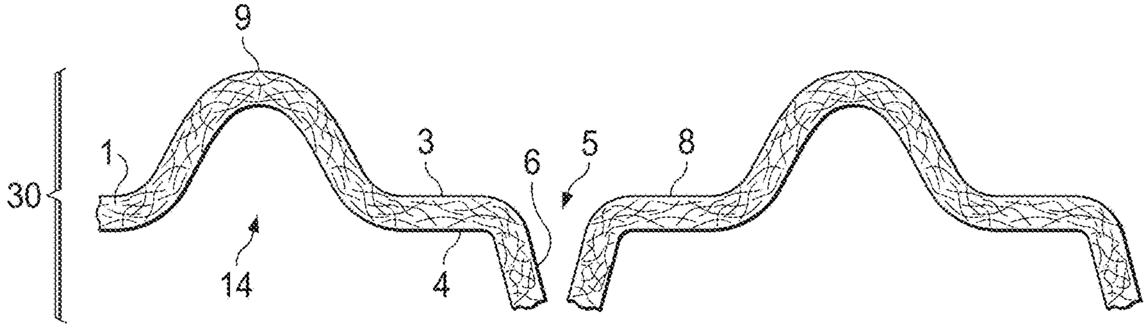
FIG. 2 is a schematic view of a nonwoven having a three-dimensional first layer in accordance with the present invention.

According to FIG. 2, the first layer 1 may comprise a plurality of protrusions 9. The first layer 1 comprises a plurality of apertures 5. The first layer 1 comprises land area 8 between the majority of the apertures 5. The land area may be substantially flat.

The majority of the protrusions 9 may protrude outwardly from the land area 8 of the first layer 1 of the nonwoven 30.

The first layer 1 has a first surface 3 and a second surface 4. The majority of the protrusions 9 may be located on the first surface 3 of the first layer 1. The majority of the protrusions 9 may extend outward from the first surface 3 of the first layer 1.

The plurality of the protrusions 9 may be uniformly distributed on the first surface 3 of the first layer 1. The plurality of the protrusions 9 may be unevenly distributed and form a shape or a pattern on the first surface 3 of the first layer 1. The majority of the protrusions 9 may be provided throughout the complete surface of the first layer 1 or may only be provided in a portion of the first layer 1.

The majority of the protrusions 9 may be surrounded by at least one land area 8 and/or a plurality of apertures 5.

The land area 8, the aperture 5 and the protrusions 9 may form a three-dimensional surface on the first surface 3 of the first layer 1 of nonwoven 30.

Alternatively, the protrusions 9 may extend outward from the second surface 4 of the first layer 1. In this case, the protrusions 9 may be named "recesses". The term "recesses" corresponds to protrusions of a topsheet that protrude away from the skin of the wearer when the topsheet is incorporated into an absorbent article. The plurality of land area 8, the plurality of apertures 5 and the plurality of protrusions 9 may form a three-dimensional surface on the second surface 4 of the first layer 1 of the nonwoven 30.

When viewing from the first surface 3 of the first layer 1, the majority of the protrusions 9 may protrude from the land area 8 of the first layer 1 in the same direction.

When the nonwoven described herein is incorporated into an absorbent article, the plurality of protrusions may protrude toward the skin of the wearer when the article is in use and away from the absorbent core of the absorbent article.

Alternatively, when the nonwoven described herein is incorporated into an absorbent article, the plurality of protrusions may protrude towards the absorbent core of the absorbent article.

Viewed from a cross-sectional view, i.e. in a Z-direction, the majority of the protrusions 9 may have any suitable shapes which include, but are not limited to: cylindrical, bulbous-shaped, conical-shaped and mushroom shaped.

Viewed from above, the majority of the protrusions 9 may have any suitable shapes which include, but are not limited to: circular, dome-shaped, diamond-shaped, round diamond-shaped, oval-shaped, clover-shaped, triangular-shaped, tear-drop shaped and elliptical-shaped protrusions.

Referring to FIG. 2, majority of the protrusions 9 may comprise an inside void volume 14 which is the portion of the protrusion which does not comprise any fibers or very little fibers. The void volume 14 can improve the breathability of the topsheet. The majority of the protrusions 9 may provide void volume to receive the body fluids.

This three-dimensional first layer of the nonwoven provides better softness to the nonwoven. It also helps maintain the skin of the wearer away from body fluids in the land area as the protrusions essentially create a space between the skin of the wearer and the body fluids when the nonwoven is incorporated into an absorbent article as a topsheet.

Second Layer:

The nonwoven of the present invention may further comprise a second layer which comprises a first surface, an opposing second surface in such a way that the first surface of the second layer is in a face to face relationship with the second surface of the first layer.

All aspects described above for the first layer are equally applicable to the second layer in nonwoven comprising a first and a second layers.

The second layer may comprise natural fibers, synthetic fibers or a combination of natural and synthetic fibers. In one embodiment, the second layer comprises thermoplastic fibers.

The list of synthetic fibers corresponds to the list disclosed above for the topsheet and the first layer.

The second layer may have a plurality of apertures at least partially aligned with the apertures of the first layer. All apertures of the second layer may be aligned with the apertures of the first layer. This may be achieved by forming the apertures of the first layer and of the second layer simultaneously after the first and second layer have been placed in a face to face relationship.

Figure 3:
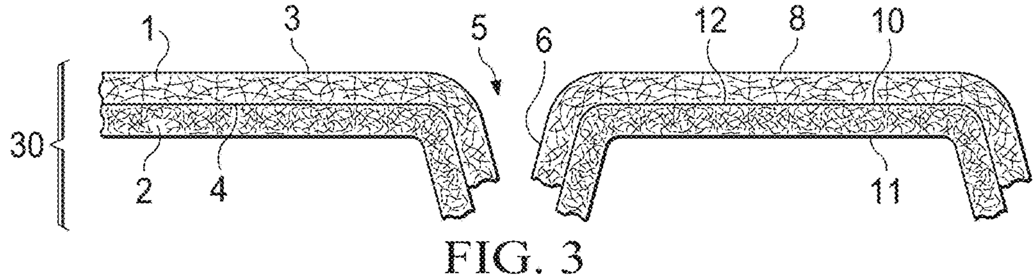
FIG. 3 is a schematic view of a nonwoven having a first layer and a second layer in accordance with the present invention.
Figure 4A:
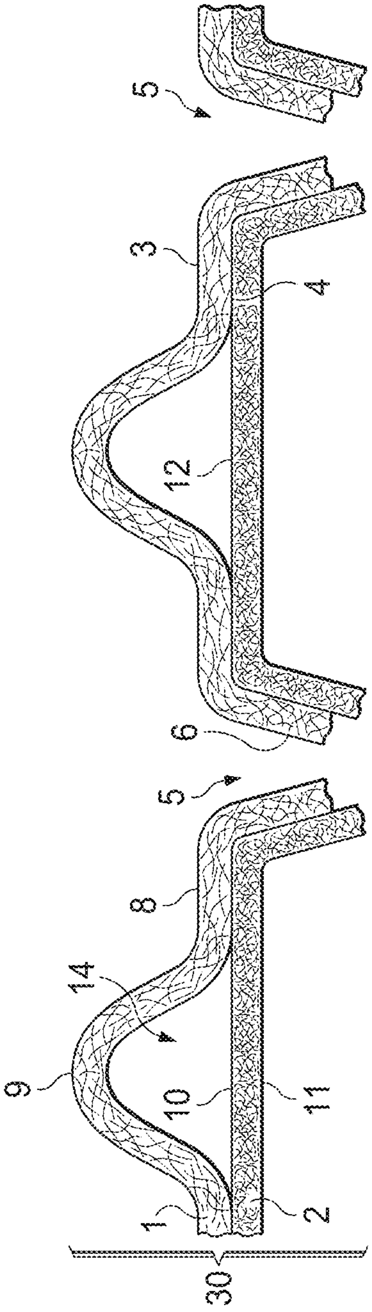
FIG. 4A is a schematic view of a nonwoven having a three-dimensional first layer and a flat second layer in accordance with the present invention.
Figure 4B:
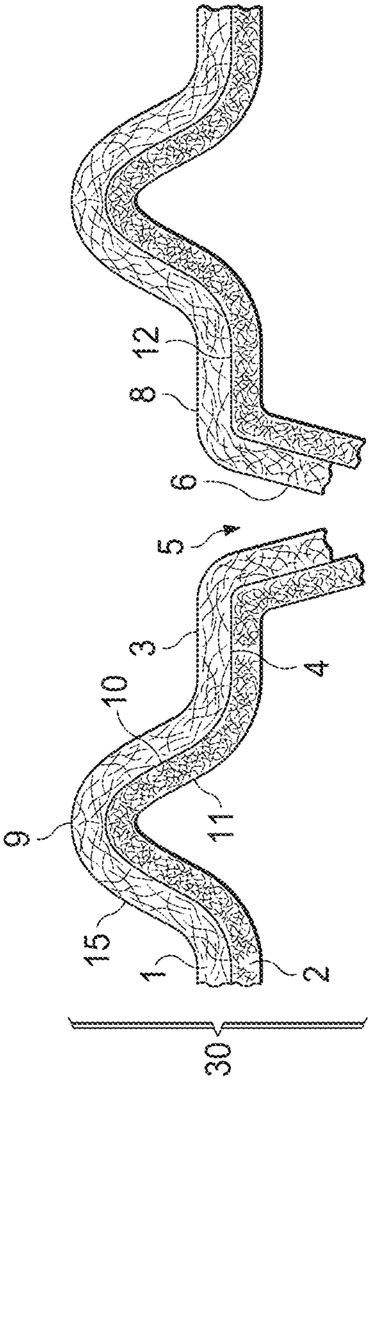
FIG. 4B is a schematic view of a three-dimensional nonwoven having a first layer and second layer in accordance with the present invention.

Referring to FIGS. 3-4B, the first layer 1 may at least partially penetrate the second layer 2 of the nonwoven 30 at the apertures 5.

This characteristic may be facilitated according to the process described below.

Alternatively, the first layer may not penetrate the second layer of the topsheet at the apertures. This characteristic may be formed by using an alternative process such as the process described in U.S. Pat. No. 5,628,097, or with a hole puncher.

Each of the apertures 5 has a side wall 6. The side wall 6 may extend outwardly, away from land area 12 of the second surface of the second layer, as shown in FIGS. 3-4B. When the nonwoven described herein is incorporated into an absorbent article, the direction of the side walls of the apertures, when extending outwardly, may be towards the absorbent core of the absorbent article. The amount of extension of the side walls of the apertures may be at least 0.1 mm beyond the second surface of the second layer, or at least 0.2 mm beyond the second surface of the second layer. The side walls of the apertures may form funnels or channels.

When the nonwoven described herein is incorporated into an absorbent article, the direction of these side walls may be towards the absorbent core of the absorbent article, or may be towards the skin of the wearer when the article is in use.

Descriptions relating to apertures correspond to the descriptions relating to apertures disclosed above for the first layer.

Referring to FIG. 3, nonwoven 30 may comprise a first layer 1 and a second layer 2. The first layer may comprise a first surface 3 and a second surface 4. The second layer may comprise a first surface 10 and a second surface 11.

The first surface 10 of the second layer 2 may be in contact with the second surface 4 of the first layer 1.

Apertures of the second layer 2 at least partially aligned, or fully aligned with the apertures 5 of the first layer 1. The apertures 5 of the first layer 1 and of the second layer 2 may be the same. The plurality of apertures 5 of the second layer 2 may have the same width and/or length as the apertures 5 of the first layer 1.

The second layer 2 may comprise land areas 12 between the majority of the apertures 5. The land area 8 of the first layer 1 may be aligned with the land area 12 of the second layer 2.

The land area 12 of the second layer 2 may fully surround the apertures 5 of the first layer 1 and of the second layer 2.

The land area 12 of the second layer 2 may be substantially flat areas.

In one embodiment, the second surface of the second layer comprises at least one non-aperture area which has no aperture and a second non-aperture area contact angle, and the second non-aperture area contact angle is not greater than the first non-aperture area contact angle.

The first layer and the second layer may be in contact with each other and may be joined with each other at the non-aperture area.

The first layer and the second layer may be joined together or attached to each other through mechanical bonding, adhesive bonding, pressure bonding, heat bonding, passing heated air through both layers, or by other methods of joining to form the topsheet known in the art.

In one embodiment, the first layer is attached to the second layer in bonding areas by hot melt adhesive. Having a hydrophilic hot melt adhesive attaching the first layer and the second layer can help to have a low run-off of liquid.

In one embodiment, first layer is partially interpenetrated to second layer in apertures. With this feature, the first layer in the side wall of an aperture having a higher contact angle may act like a barrier against fluid-back from the second layer and the absorbent core, so that rewet caused by fluid-back from the second layer and the absorbent core may be mitigated or prevented.

Referring to FIG. 3, in addition, the second layer may not be not completely covered by the first layer in the apertures, and be exposed in an area of the apertures proximate to the bottom edge of the aperture. Having such a feature, even though the first layer in the apertures has a higher contact angle, the second layer in the apertures having a lower contact angle and hydrophilic still helps liquid to pass through the apertures.

Referring to FIG. 4A, the nonwoven 30 may comprise a three-dimensional first layer 1 and a flat second layer 2. The first layer may comprise a first surface 3 and a second surface 4. The second layer comprises a first surface 10 and a second surface 11. The first surface 10 of the second layer 2 may be in contact with and joined to the second surface 4 of the first layer 1.

The first layer 1 may have a plurality of protrusions 9 protruding from the land area 8 of the first layer 1 of the nonwoven 30. The majority of the protrusions 9 may comprise an inside void volume 14 which is the portion of the protrusion which does not comprise any fibers or very little fibers. The void volume 14 can improve the breathability of the topsheet.

Referring to FIG. 4B, the nonwoven 30 may be a laminate comprising the first layer 1 as previously described and a second layer 2 as previously described in a face to face relationship. The nonwoven 30 may be a composite nonwoven having a unitary structure comprising the first layer and a second layer. A unitary structure herein intends to mean that although it may be formed by several sub-layers that have distinct properties and/or compositions from one another, they are somehow intermixed at the boundary region so that, instead of a definite boundary between sub-layers, it would be possible to identify a region where the different sub-layers transition one into the other. Such a unitary structure is typically built by forming the various sub-layers one on top of the other in a continuous manner, for example using air laid or wet laid deposition.

The first layer 1 and the second layer can be simultaneously mechanically deformed and combined to provide the topsheet having apertures and optional protrusions. This means that both the first layer 1 and the second layer 2 can be mechanically deformed and combined at the same time.

When the first layer and the second layer comprise a plurality of protrusions 9, the plurality of protrusions 9 of the first layer may be at least partially aligned, or fully aligned with the plurality of protrusions 9 of the second layer 2. The protrusions 9 of the first layer 1 and of the second layer 2 may be the same.

The first layer 1 and the second layer 2 may comprise a plurality of recesses. The apertures 5 may be located between the majority of the recesses and/or within the majority of recesses. Some recesses may not have apertures 5 therein.

The plurality of recesses of the first layer may be aligned with the plurality of recesses of the second layer. The plurality of recesses of the first layer and of the second layer may be the same. The first layer and the second layer may be in contact with each other at the recesses.

When the nonwoven described herein is incorporated into an absorbent article, the first surface 3 of the first layer 1 is facing towards the body of the wearer during use of the article and the second surface 4 of the first layer 1 is facing towards the backsheet. When the topsheet comprises a first layer 1 and a second layer 2, the first layer 1 is facing towards the body of the wearer and the second layer 2 is facing towards the backsheet.

Absorbent Article

Figure 5:
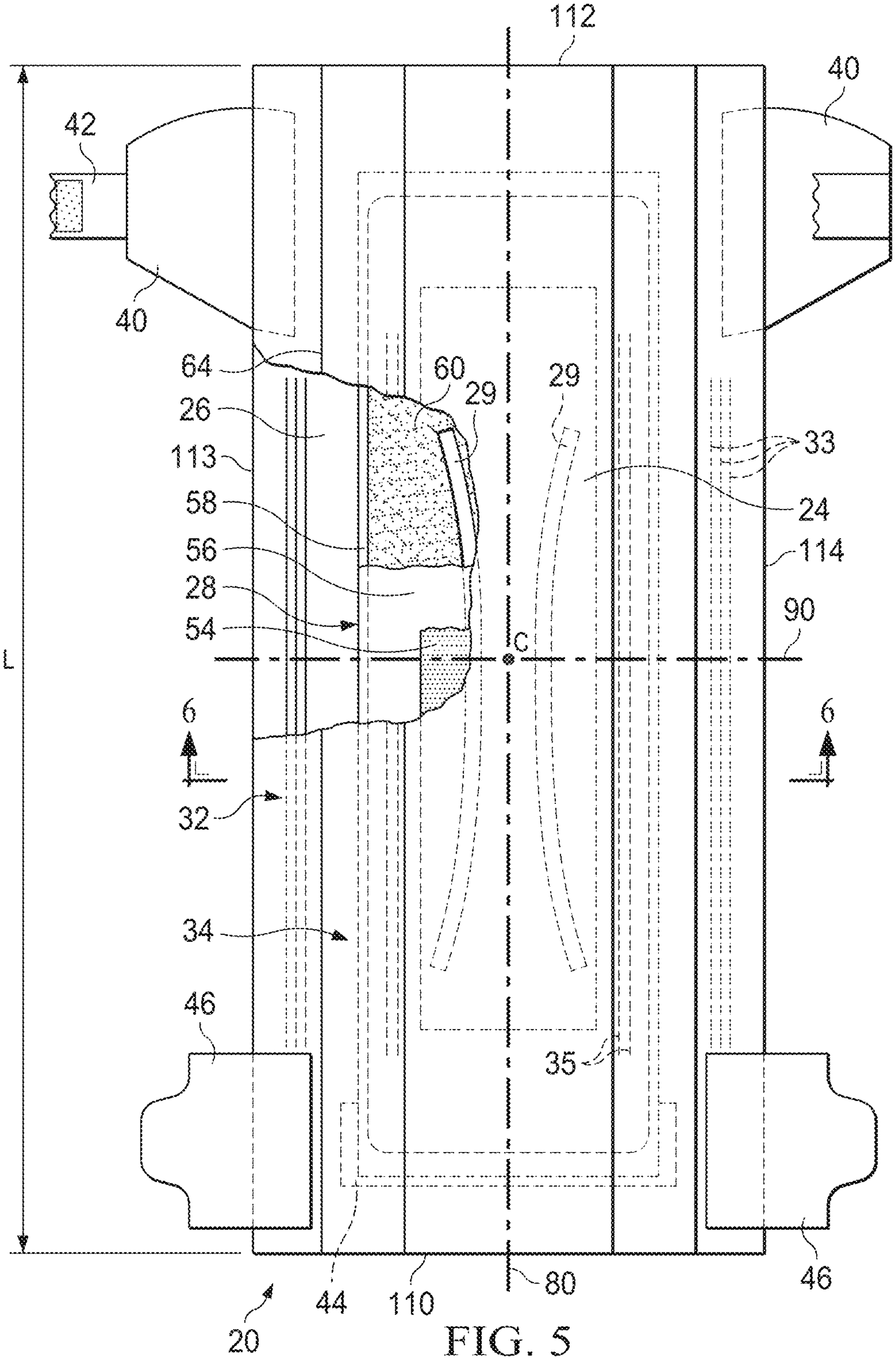
FIG. 5 is a perspective view of an exemplary absorbent article.

Absorbent articles will be generally further illustrated in the form of a baby diaper 20 as exemplarily represented in FIG. 5. FIG. 5 is a plan view of the exemplary diaper 20 in a flattened-out configuration with the taped ends opened and the garment-facing side turned up. An article that is presented to the user closed such as a training pant may also be represented flattened out by cutting it along its side waists. The absorbent article will typically have a front edge 110, a back edge 112 and the longitudinally-extending lateral side edges 113, 114. The front edge 110 forms the edge of the front waist and the back edge 112 of the back waist, which together when worn by the wearer form the opening for the waist of the wearer. The lateral edges 113, 114 can each form one of the leg openings. The absorbent article 20 notionally comprises a longitudinal centerline 80 dividing the article in a left side and a right side, and a perpendicular transversal centerline 90 disposed at half the length of the article as measured on the longitudinal centerline 80, with both centerlines crossing at the center point C. The taped back ends 42 attached on the front of the diaper to such as a landing zone 44.

Figure 6:
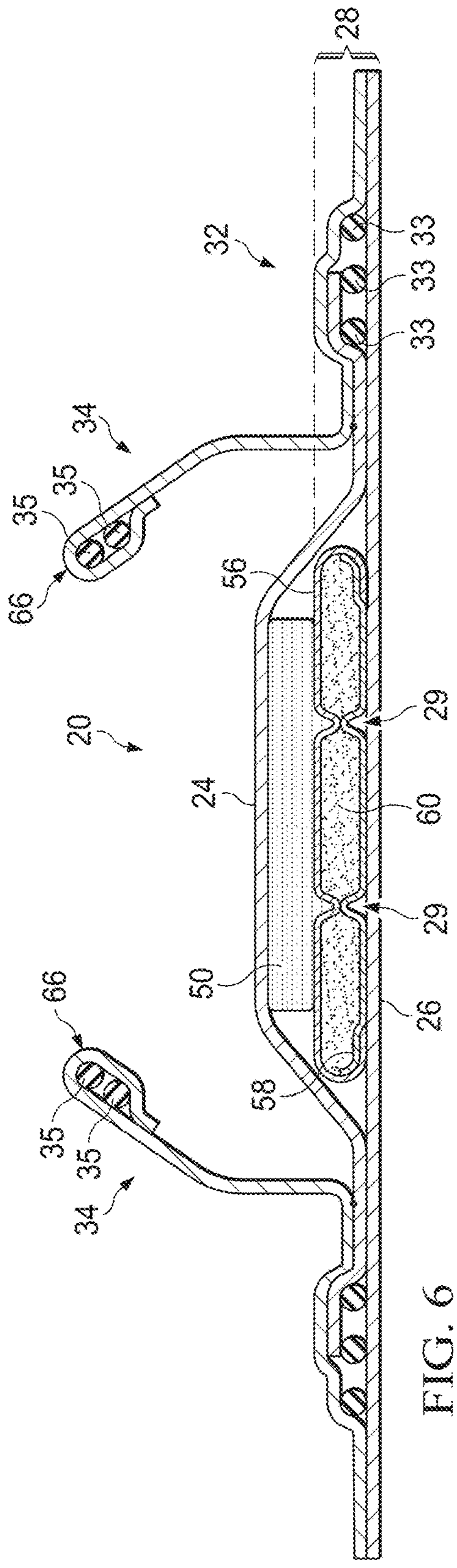
FIG. 6 is a lateral cross-section view along 6-6 of the absorbent article of FIG. 5.

Other layers of the absorbent article are better illustrated in FIG. 6, which shows in cross-section in addition to the liquid permeable topsheet 24 and the backsheet 26, an absorbent core 28 between the topsheet 24 and the backsheet 26.

An optional acquisition and/or distribution layer (or system) 50 is represented in FIG. 6 together with other typical diaper components. The acquisition and/or distribution layer may comprise one layer or more than one layer. Typical acquisition and/or distribution layers may not comprise SAP as this may slow the acquisition and distribution of the fluid, but an additional layer may also comprise SAP if some fluid retention properties are wished.

The absorbent article may typically comprise a pair of partially upstanding barrier leg cuffs 34 having elastic elements 35 and elasticized gasketing cuffs 32 having elastic elements 33 substantially planar with the chassis. Both types of cuffs are typically joined to the chassis of the absorbent article typically via bonding to the topsheet and/or backsheet.

The absorbent article may comprise elasticized back ears 40 having a tape end 42 which can be attached to a landing zone 44 at the front of the article, and front ears 46 typically present in such taped diapers.

Figure 7:
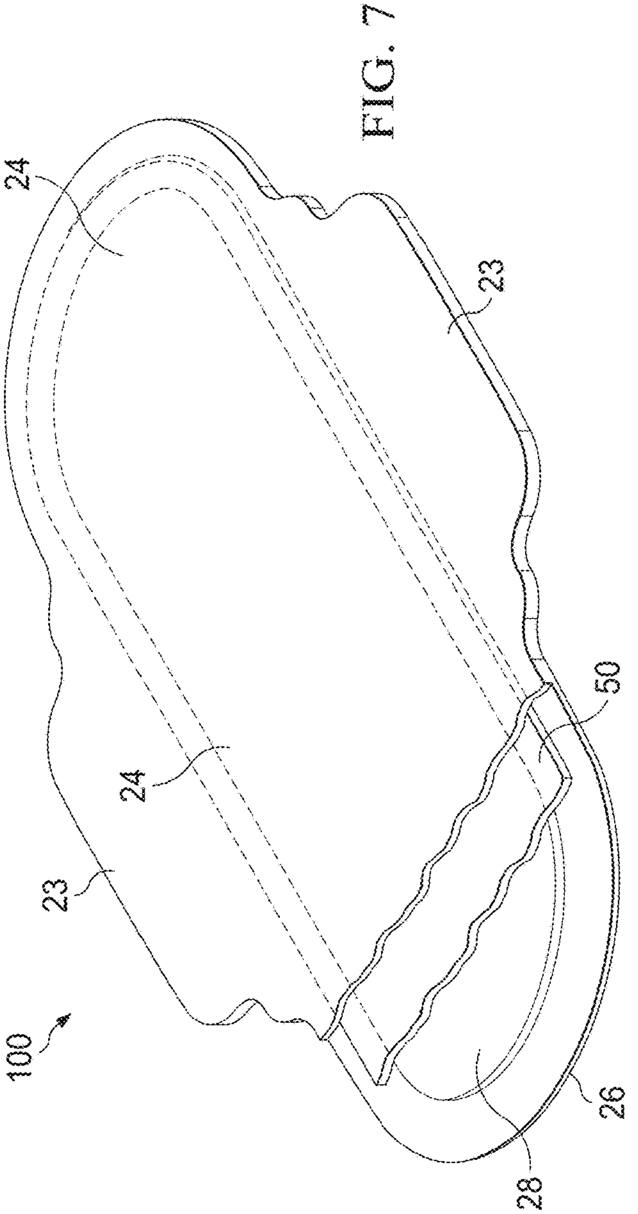
FIG. 7 is a schematic plan view of an exemplary absorbent article.

Absorbent articles will also be generally discussed and further illustrated in the form of a sanitary napkin 100 as exemplarily represented in FIG. 7 which is a plan view of the exemplary sanitary napkin 100 in a flattened-out configuration and the wearer facing side turned up. As shown in FIG. 7, an absorbent article according to the present invention, a sanitary napkin 100 for example, comprises a topsheet 24 having a wearer facing surface and a garment facing surface (not shown in FIG. 7) positioned opposite to the wearer facing surface. The absorbent article further comprises a backsheet 26 having a garment facing surface and a user facing surface positioned oppositely to the garment facing surface, the backsheet 26 being at least partially joined to the topsheet 24. The absorbent article also comprises an absorbent core 28 positioned between the topsheet 24 and the backsheet 26. The absorbent article may further comprise an optional acquisition and/or distribution layer (or system) or a secondary topsheet 50 is represented and/or a pair of flaps or wings 23. The topsheet 24, the backsheet 26, and the absorbent core 28 can be assembled in a variety of well-known configurations.

The backsheet 26 and the topsheet 24 can be secured together in a variety of ways. The topsheet 24 and the backsheet 26 can be joined to each other by using an adhesive, heat bonding, pressure bonding, ultrasonic bonding, dynamic mechanical bonding, or a crimp seal. A fluid impermeable crimp seal can resist lateral migration ("wicking") of fluid through the edges of the product, inhibiting side soiling of the user's undergarments.

When the absorbent article is a sanitary napkin as shown in FIG. 7, as is typical for sanitary napkins and the like, the sanitary napkin can have panty-fastening adhesive disposed on the garment facing side of backsheet 26. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the user's panties.

Topsheet

A topsheet is generally liquid permeable and is configured to receive the fluids being excreted from the body and aid in directing the fluids toward an acquisition/distribution layer (system), and/or the absorbent core. One of the important qualities of a topsheet is the ability to reduce ponding of the fluids on the topsheet before the fluids are able to be absorbed by the absorbent article. Another desirable quality of a topsheet is to reduce rewet of the topsheet to provide dry sensory feel. In addition, a topsheet with a low run-off to prevent fluid leakage is also desired.

The topsheet may be joined to portions of the backsheet, the absorbent core, and/or any other layers as is known to those of ordinary skill in the art. Further, at least a portion of, or all of, the topsheet may be liquid permeable, permitting liquid bodily exudates to readily penetrate through its thickness.

The topsheet in the absorbent article of the present invention comprises the nonwoven according to the present invention, and is free from cellulose-based fibers. The topsheet may be formed of a single layer, of two layers, or, of more than two layers.

Absorbent Core

As used herein, the term "absorbent core" refers to a component used or intended to be used in an absorbent article and which comprises an absorbent material and optionally a core wrap. As used herein, the term "absorbent core" does not include the topsheet, the backsheet and any acquisition-distribution layer or multilayer system, which is not integral part of the absorbent core. The absorbent core is typically the component of an absorbent article that has the most absorbent capacity of all the components of the absorbent article. The terms "absorbent core" and "core" are herein used interchangeably. The absorbent core can be manufactured in a wide variety of sizes and shapes, and may be profiled to have different caliper, hydrophilic gradients, superabsorbent gradients, densities, or average basis weights at different positions across the face of the product.

Referring to FIGS. 5-7, the absorbent core 28 can absorb and contain liquid received by the absorbent article and comprise an absorbent material 60 (not indicated in FIG. 7). Referring to FIGS. 5 and 6, The absorbent core 28 may comprise absorbent material free channels 29, through which the top side 56 of the core wrap may be bonded to the bottom side 58 of the core wrap. Of course, this is entirely optional, the absorbent core may also not have bonded channels, or even unbonded channels. The absorbent core may be rectangular, but it is also common to have a shaped area which is tapered in the area around the transversal centerline 90.

The absorbent material comprises a liquid-absorbent material commonly used in disposable absorbent articles such as comminuted wood pulp, which is generally referred to as airfelt or fluff. Examples of other suitable liquid-absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials.

The absorbent material in the absorbent core can be any type. It can be an airfelt core comprising wood cellulose fibers such as pulp fibers mixed with SAP, or an airfelt-free core free from such cellulose fibers. Airfelt cores typically comprises from 40% to 80% of SAP. For absorbent cores comprising a relatively high proportion of SAP at least partially enclosed within the core wrap, the SAP content may represent in particular at least 80%, 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent core may comprise an absorbent material comprising at least 80%, at least 90%, at least 95%, or at least 99% by weight of the absorbent core. The term "superabsorbent polymer" (herein abbreviated as "SAP") refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it not excluded that other forms of SAP may be used such as a superabsorbent polymer foam for example.

Backsheet

A backsheet that covers the lower side of the absorbent core prevents the fluids in the absorbent core from wetting articles that contact the sanitary napkin, such as undergarments. Accordingly, the backsheet can be made from a liquid impervious thin film or a liquid impervious but vapor pervious film/nonwoven laminate, a microporous film, an apertured formed film, or other polymer film that is vapor permeable, or rendered to be vapor permeable, but substantially impervious to fluid.

Outer Cover.

An outer cover, not indicated in the drawings, may cover at least a portion of, or all of, the backsheet 26 to form a soft garment-facing surface of the absorbent article. The outer cover may be formed of one or multi-layered nonwoven. The nonwoven can comprise a combination of natural fibers and synthetic fibers that are not natural fibers.

Method for Nonwoven Treatment with a Treatment Composition

When apertures in nonwoven comprise a treatment, the treatment may be applied to the nonwoven using a well known method such as pin aperturing processes and via printing processes. The treatment may be applied to the nonwoven simultaneously with aperture formation on the nonwoven using, for example, pin aperturing process comprising steps of: a) providing a first layer comprising a first surface and an opposite second surface, b) providing an aperturing apparatus comprising a first forming member and a second forming member which engages the first forming member, wherein the first forming member comprises a plurality of pins on its surface and the second forming member comprises a plurality of recesses on its surface, c) wetting the pins on the first forming member with a treatment, and d) moving the first layer between the first and second forming members so that apertures are formed in the first layer as the pins on the first forming member and the recesses on the second forming member are engaged and the apertures are treated with the treatment. When a nonwoven comprises a first layer and a second layer, a first layer comprising a first surface and an opposite second surface, and a second layer comprising a first surface and an opposite second surface are provided in such a way that the first surface of the second layer is in a face to face relationship with the second surface of the first layer to step d) so that apertures are formed on both the first layer and the second layer in step d).

Figure 8:
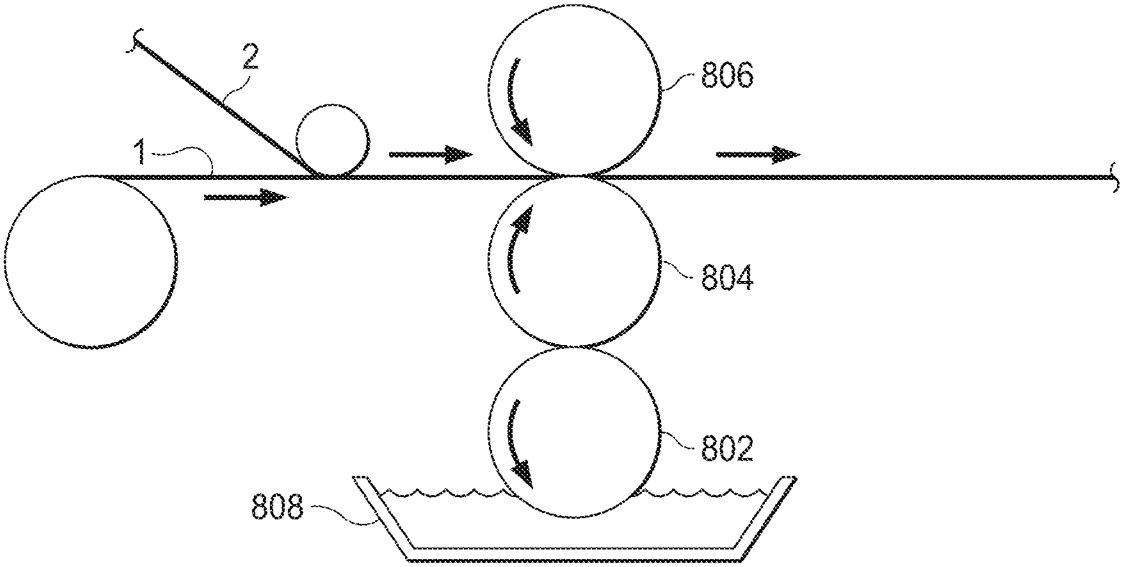
FIG. 8 is a schematic illustration of an apparatus for applying a treatment to a nonwoven.

For example, aperturing pins process forming apertures and treating the apertures with a treatment may correspond to a process having three rolls wherein a first roll picks up the treatment from a container containing the treatment and transfers it to an intermediate roll comprising aperture forming elements. The intermediate roll intermeshes with a third roll to form apertures on a nonwoven and while wetting side walls of the apertures. The excess of hydrophobic surfactant may be removed with a vacuum roller. Referring to FIG. 8, a treatment composition is prepared and stored in a soaking tank 808. A first roll 802 is disposed in the soaking tank 808 so as to be at least partially submerged in the treatment in the soaking tank 808, so that, as the first roller 802 passes through the treatment, an amount of the treatment may be picked up and carried in in the surface of the first roller 802. The first roller 802 may comprise resilient or compressible surface such as rubber to effectively hold a certain amount of the treatment. A first forming member, a second roll 804 in this case, comprises a plurality of aperture-forming elements such as pins. A second forming member, a third roll 806 in this case, comprises a plurality of recesses. The aperture-forming elements in the first forming member 804 intermesh with the recesses in second forming member 806. A first layer 1 from a spool or otherwise is fed between a first forming member 804 and second forming member 806. As the first nonwoven layer is fed between the first forming member 804 and second forming member 806, the first forming member 804 may bring the first nonwoven layer 1 into contact with the aperture-forming elements of the first forming member 804 and the treatment thereon. Upon contact of the first nonwoven layer 1 with the aperture-forming elements of the first forming member 804, the first forming member 804 together with second forming member 806 create apertures in the first nonwoven layer 1 while wetting the side walls of the apertures with the treatment. Optionally a second layer 2 from a spool or otherwise may be fed together with the first layer 1 between a first forming member 804 and second forming member 806 in such a way that the first layer 1 and the second layer 2 are in a face to face relationship so that apertures are formed through the first layer 1 and the second layer 2 and side walls of the apertures are coated with the treatment.

The treatment may have a HLB value not higher than about 13.

By treating the apertures with treatment with a HLB value not higher than about 13 which results in areas such as peripheries and sidewalls of the apertures being coated with the treatment, the coated areas become hydrophobic or less hydrophilic than the non-aperture area of the first surface of the first layer. The fluid is less likely to be absorbed by fibers or trapped between fibers in these areas which can lead to reduction of fluid rewet and a stain size. On the other hand, the non-aperture area remains hydrophilic, and impact on acquisition speed is minimized.

Therefore, the topsheet as disclosed herein can provides a reduced rewet and clear surface onto the wearer-facing surface of the absorbent article without compromising fast liquid acquisition.

Measurement

1. Contact Angle Test

Figure 9:
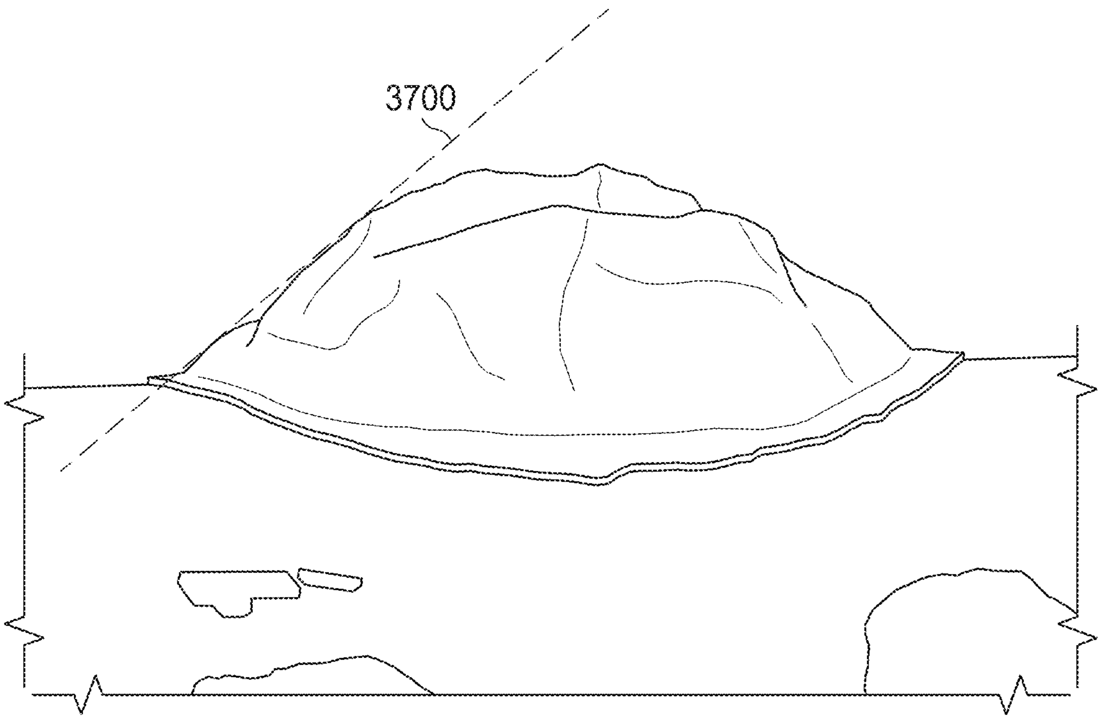
FIG. 9 is a photomicrograph depicting exemplary water droplet on fibers for the contact angle test method disclosed herein.
Figure 10:
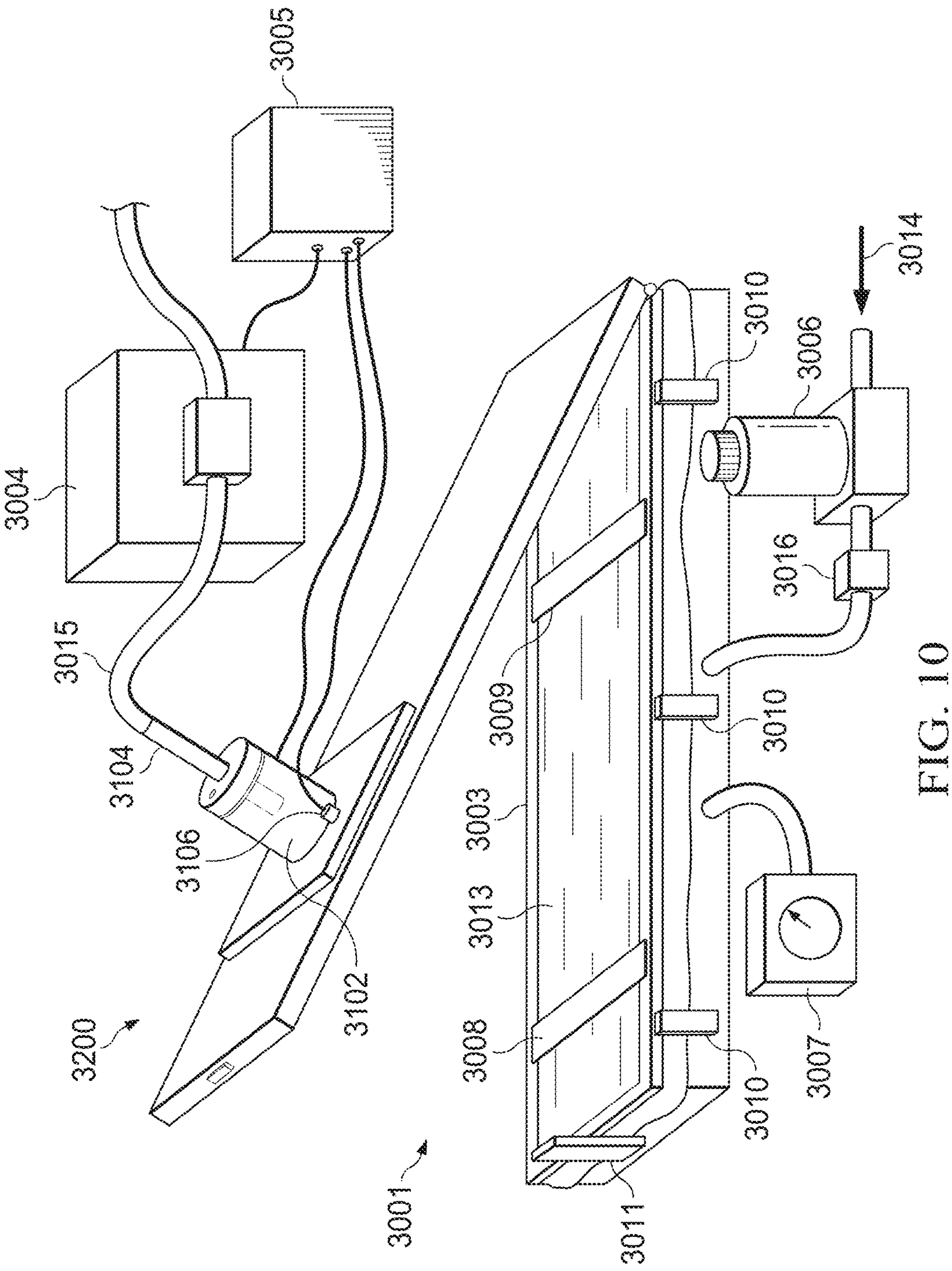
FIG. 10 illustrates an apparatus used in the Modified Fluid Acquisition Test.

A rectangular specimen measuring 1 cm×2 cm is cut from a law material nonwoven or a topsheet of a disposable absorbent product taking care not to touch the surface of the specimen or to disturb the structure of the material. The specimen has a length of (2 cm) aligned with a longitudinal centerline of the article. The specimen is handled gently by the edges using forceps and is mounted flat with the skin-facing side up on an SEM specimen holder using double-sided tape and secured with carbon cement. The specimen is sprayed with a fine mist of water droplets generated using a small hobby air-brush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a *Quorum* PP3010T Cryo-SEM prep chamber at −150° C., coated with Pt, and transferred into Hitachi Ethos NX5000 Cryo-SEM chamber at −150° C. The Hitachi Ethos NX5000 Cryo-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. The contact angle between the droplet and the fiber is determined directly from the image taken as is shown via lines 3700 in FIG. 9.

Such method is performed on the non-aperture area of the first surface of the first layer to measure the first non-aperture area contact angle. Ten separate droplets, located on the non-aperture area in the middle between two neighboring apertures, are imaged from which twenty contact angle measurements are performed (one on each side of each imaged droplet), and the arithmetic average of these twenty contact angle measurements is calculated and reported as the first non-apertured area contact angle.

Such method is also performed on the apertures to measure the aperture contact angle. Ten separate droplets, located near the top of three separate apertures, and ten droplets, located near the bottom of the same three separate apertures, are imaged from which forty contact angle measurements are performed (one on each side of each imaged droplet), and the arithmetic average of these forty contact angle measurements is calculated and reported as the aperture contact angle.

2. Modified Fluid Acquisition Test

The Modified Fluid Acquisition ("MFA") Test is designed to measure the speed at which 0.9% saline solution is absorbed into an absorbent article that is compressed at 2.07 kPa. A known volume is introduced four times, each successive dose starting five (5) minutes after the previous dose has absorbed. Times needed to absorb each dose are recorded. The test fluid is 0.9% w/v saline solution and is prepared by weighing 9.0 g±0.05 g of NaCl into a weigh boat, transferring it into a 1 L volumetric flask, and diluting to volume with de-ionized water.

The MFA apparatus is depicted in FIG. 10 through FIG. 12B. The MFA apparatus comprises a bladder assembly 3001 and a top plate assembly 3200 that includes a deposition assembly 3100. A controller 3005 is used to 1) monitor the impedance across electrodes 3106, recording the time interval 0.9% saline solution is in a cylinder 3102, 2) interface with a liquid pump 3004 to start/stop dispensing, and 3) time intervals between dosing. The controller 3005 is capable of recording time events to ±0.01 sec. A house air supply 3014 is connected to a pressure regulator 3006 capable of delivering air at a suitable flow/pressure to maintain 2.07 kPa in the bladder assembly 3001. A liquid pump 3004 (Ismatec MCP-Z gear pump, available from Cole Palmer, Vernon Hills, IL or equivalent) capable of delivering a flow of 10-80 mL at a rate of 3-15 mL/s is attached to a steel tube 3104 of the deposition assembly 3100 via tygon tubing 3015.

The bladder assembly 3001 is constructed of 12.7 mm Plexiglas with an overall dimension of 80 cm long by 30 cm wide by 10 cm tall. A manometer 3007 to measure the pressure inside the assembly and a pressure gauge 3006 to regulate the introduction of air into the assembly are installed through two holes through the light side. A bladder 3013 is assembled by draping a 50 mm by 100 mm piece of silicone film, (thickness 0.02", Shore A durometer value of 20, available as Part #86435K85 from McMaster-Carr, Cleveland, OH) over the top of the box with enough slack that the film touches the bottom of the box at its center point. An aluminum frame 3003 with a flange is fitted over the top of the film and secured in place using mechanical clamps 3010.

When in place, the assembly should be leak free at a pressure of 3.45 kPa. A front 3008 and back 3009 sample support of 5 cm by 30 cm by 1 mm are used to anchor the sample. The absorbent article is attached to the top surface of the sample supports by either adhesive tape or mechanical "hook" fasteners. These supports can be adjusted along the length of the aluminum frame 3003 via a simple pin and hole system to accommodate different size absorbent articles and to correctly align their loading point.

Figure 12B:
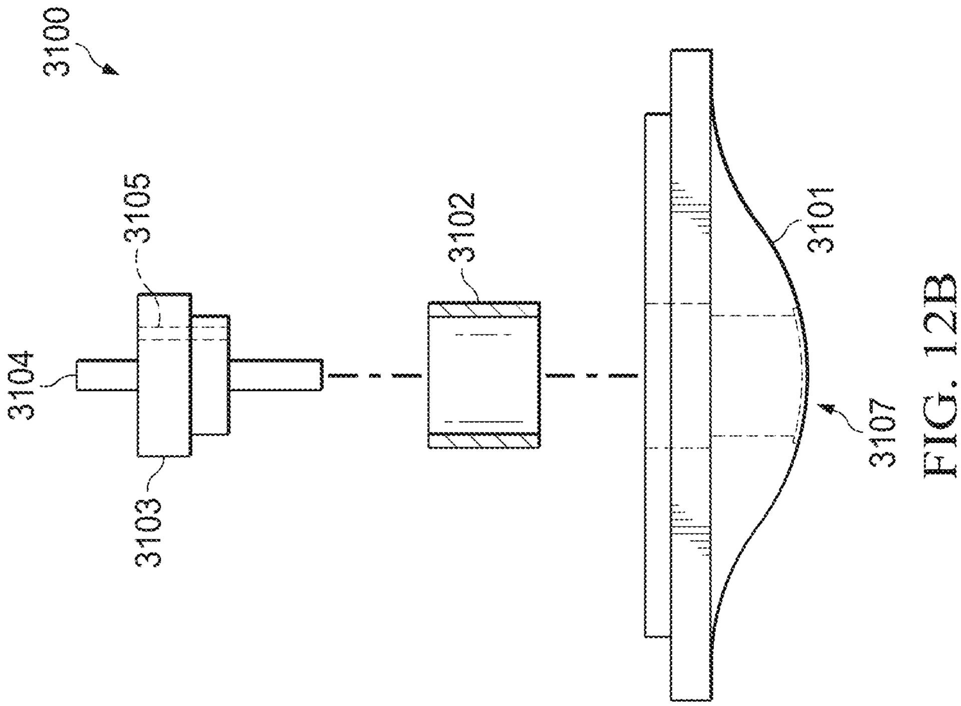
FIG. 12B illustrates equipment used in the Modified Fluid Acquisition Test.
Figure 12A:
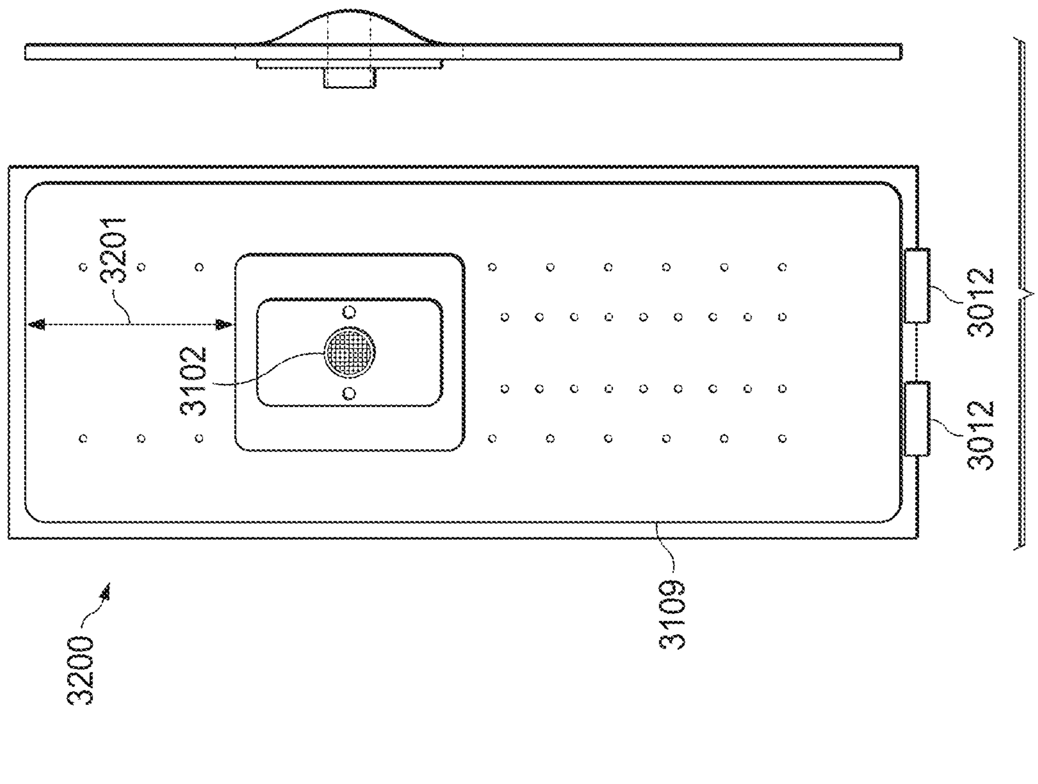
FIG. 12A illustrates a top plate assembly used in the Modified Fluid Acquisition Test.

The top plate assembly 3200 is constructed of an 80 cm by 30 cm piece of 12.7 mm Plexiglas reinforced with an aluminum frame 3109 to enhance rigidity. The plate has a cutout 170 mm wide by 201 mm long centered laterally on the plate, 170 mm from the front of the plate 3201 for mounting of the deposition assembly. In addition, the top plate has thirty-six (36) 3.2 mm diameter holes drilled through it distributed as shown in FIG. 12A. The holes prevent air from being trapped under the top plate as the bladder is inflated. The top plate assembly 3200 is connected to the bladder assembly 3001 via two hinges 3012. During use, the top assembly is closed onto the bladder assembly and locked into place using a mechanical clamp 3011.

Figure 11A:
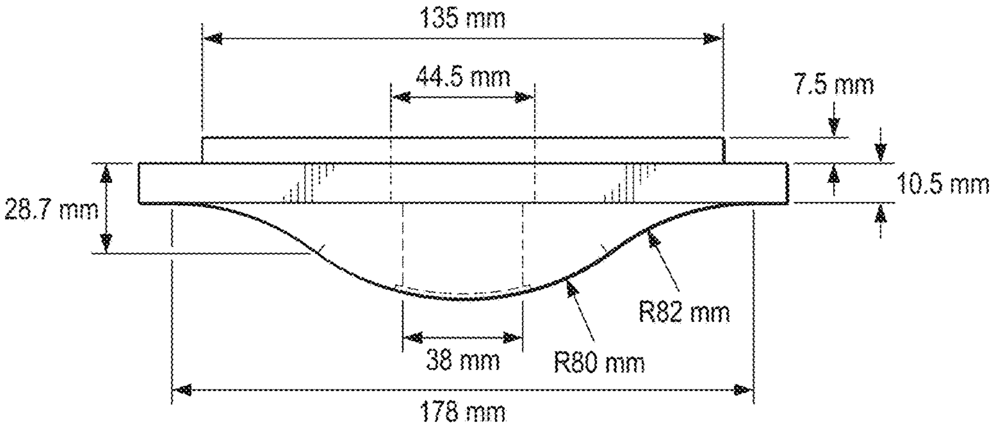
FIG. 11A is a side view of the curved component used in the Modified Fluid Acquisition Test.
Figure 11B:
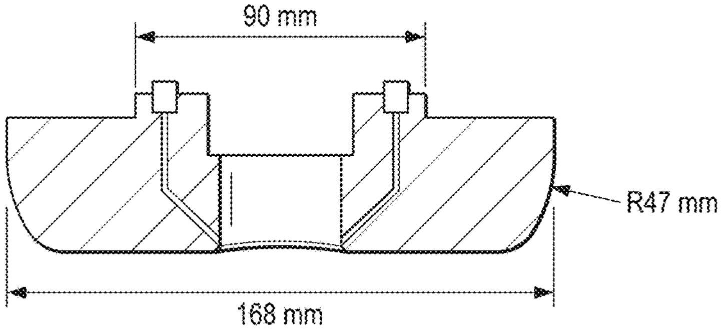
FIG. 11B is an end view of the curved component of FIG. 11A.
Figure 11C:
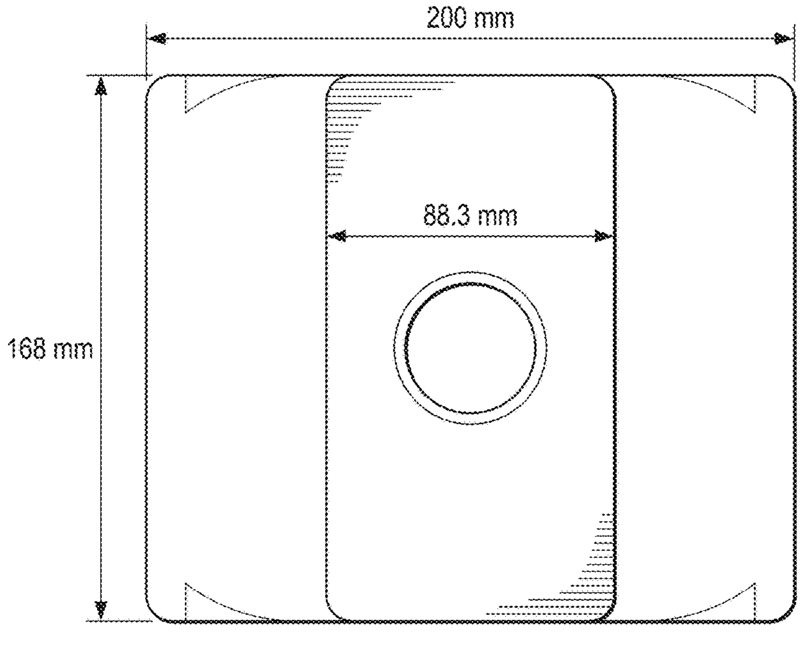
FIG. 11C is a bottom view of the curved component of FIG. 11A.
Figure 11D:
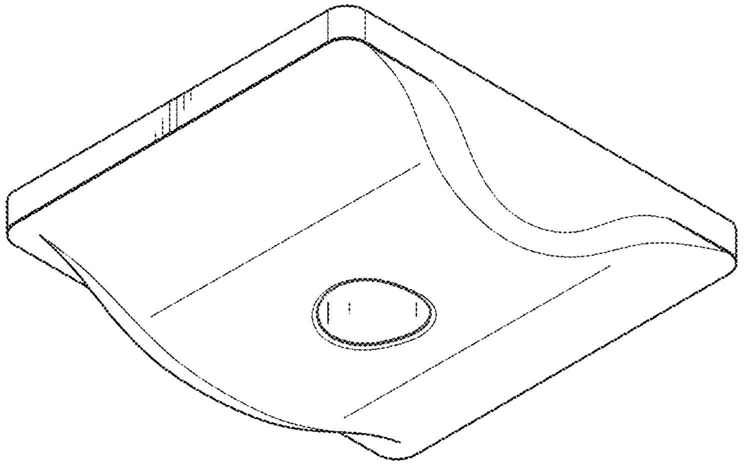
FIG. 11D is a bottom perspective view of the curved component of FIG. 11A.
Figure 11E:
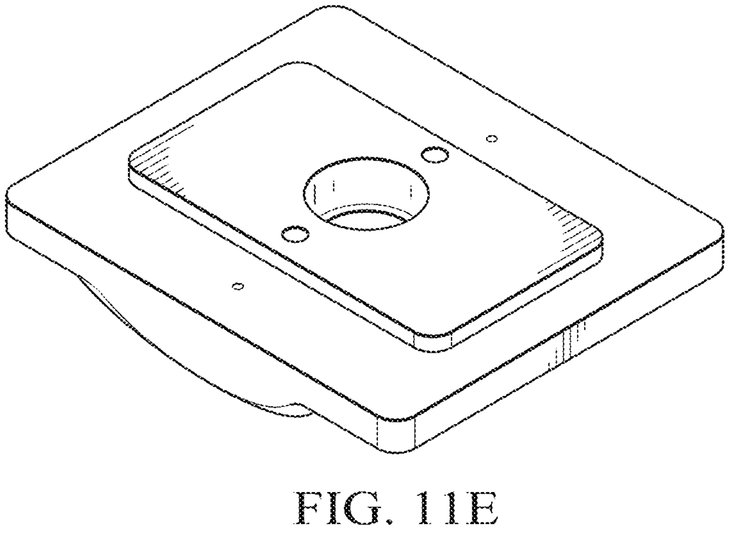
FIG. 11E is a top perspective view of the curved component of FIG. 11A.

The deposition assembly 3100 is fitted into the top plate 3200 and includes 1) a liquid introduction cylinder 3102, 2) a curved surface 3101 at the loading point of the absorbent article and 3) electrodes 3106 that are used to detect fluid in the cylinder 3102. The detailed dimensions of the curved component are provided in FIG. 11A to FIG. 11E. FIG. 11A is a side view of the curved component. FIG. 11B is an end view of the curved component. FIG. 11C is a bottom view of the curved component. FIG. 11D is a bottom perspective view of the curved component. FIG. 11E is a top perspective view of the curved component. This curved component can be milled or 3D printed. The top portion of the introduction cylinder is a 50.8 mm O.D. Plexiglas cylinder 3102 with a 38.1 mm I.D. This is fitted into the curved component to give the introduction cylinder a total height of 100 mm. Imbedded electrodes run from connectors on the upper surface of the curved component and terminate flush with an inside wall of the introduction cylinder, 2 mm from the bottom of the cylinder. The two electrodes are positioned 180 degrees apart. A nylon screen 3107 is cut and affixed flush with the bottom of the cylinder such that the sample cannot swell into the cylinder. A 5 mm semi-circle is cut in the screen in the immediate area of the two electrodes. The deposition assembly is inserted into the top plate as shown in FIG. 12A such that the curved surface is flush with the bottom of the top-plate assembly 3200. The introduction cylinder 3102 is topped with a loose-fitting nylon cap 3103. The cap has a 6.35 mm O.D. steel tube 3104 inserted through its center. When the cap is in place, the bottom of the tube ends 20 mm above the screen 3107. The cap also has an air hole 3105 to ensure negative pressure does not impede the absorption speed.

The absorbent article is first prepared by excising any inner or outer leg cuffs, waist caps, elastic ears or side panels, taking care not to disturb the topsheet that resides above the article's core region. Place the absorbent article flat onto a lab bench and identify the intersection of the longitudinal centerline with the size dependent loading point as defined in Table 1.

TABLE 1

Conditions for Modified Fluid Acquisition Testing:

| | Approximate | Loading Point from front of Core* | | Single Dose | Flow |
|---|---|---|---|---|---|
| Diaper Size | Baby Weight Pounds | Boy mm | Girl mm | Volume mL | Rate mL/s |
| 1 | 8 to 13 | 64 | 64 | 24 | 8 |
| 2 | 13 to 17 | 76 | 89 | 24 | 8 |
| 3 | 17 to 28 | 89 | 114 | 50 | 10 |
| 4-6 | 28+ | 102 | 127 | 75 | 15 |

*the boy loading point is used for unisex diapers.

Attach the front end of the absorbent article to the top surface of the front sample plate 3008 by either adhesive tape or mechanical "hook" fasteners with a topsheet facing upward. The placement is such that just the chassis and not the absorptive core overlays the plate. The sample plate 3008 is attached to the aluminum frame 3003 such that the size-dependent Loading Point (as defined in Table 1) of the absorbent article will be centered longitudinally and laterally within the cylinder 3102 when the top plate assembly has been closed. The back end of the absorbent article is secured to the back sample plate 3009 by either adhesive tape or mechanical "hook" fasteners, once again ensuring that only the chassis and not the absorptive core overlays the plate. The back sample plate 3009 is then attached to the aluminum frame 3003 such that the article is taunt but not stretched. The top plate assembly is closed and fastened, and the bladder is inflated to 2.07 kPa±0.07 kPa. The pressure is maintained at this level during the complete loading sequence of the test.

The pump 3004 is primed and then calibrated to deliver the size-dependent volume and flow rate selected from Table 1. Volume and flow rate must be within ±2% of target. The cap 3103 is placed into the cylinder 3102. The controller 3005 is started, which in turn delivers the first dose of 0.9% saline solution. After the volume has been absorbed, the controller waits for 5.0 minutes before addition of the next dose. This cycle is repeated for a total of four doses. If the fluid leaks out of or around the article (i.e., is not absorbed into the article) then the test is aborted. Also if any acquisition time exceeds 1200 seconds, the test is aborted. The acquisition time is defined as the difference between the start time (i.e., when the 0.9% saline is first introduced into the cylinder and that conducting fluid completes the circuit between the electrodes) and the stop time (i.e., when the fluid has completely drained from the cylinder and the circuit between the electrodes is broken). Acquisition times are recorded by the controller for each dose to the nearest 0.01 second. After the last dose is acquired, pressure is applied for an additional 10 minutes. Open the pressure relief valve 3016 to deflate the bladder and then remove the sample from the acquisition system.

In like fashion, run a total of eight (8) replicates for each absorbent article to be evaluated. Calculate and report the Acquisition Times (sec) for each dose as the arithmetic mean of the replicates to the nearest 0.01 sec.

3. Collagen Rewet Test

The Collagen Rewet Test is performed immediately after the MFA Test. The Collagen Rewet Test comprises measuring the mass of fluid expressed from an absorbent article under pressure after loading by the MFA protocol. Collagen sheets are used as the rewet substrate. A suitable collagen is Naturin Coffi collagen sheets (available Naturin GmbH & KG, Germany) or equivalent. Upon receipt, the collagen sheets are stored at about 23° C.±2 C.° and about 50%±2% relative humidity for 2 hours prior to testing. Equipment for the test consists of a Plexiglas disk 70.0 mm in diameter and 20 mm thick and a stainless steel confining weight that rests upon it. The mass of the disk and confining weight combined is 9100 g±2 g which corresponds to a pressure of 23.2 kPa. Collagen sheets are die cut into 70.0 mm diameter circles and stacks of four (4) assembled for use during rewet testing. Measure and record the mass of the dry filter paper stack and record to the nearest 0.0001 g.

Within 30 seconds after the conclusion of the MFA test, remove the absorbent article from the acquisition apparatus and place it flat on a bench top with a topsheet facing upward. Then, place a pre-weighed stack of collagen centered at the loading point (as determined previously in the MFA test), place the Plexiglass disk onto the stack, and gently place the confining weight onto the disk. Wait for 15.0 seconds±0.5 seconds and remove the weight and disc. Immediately measure the mass of the wet filter paper and record to the nearest 0.0001 g. Calculate the Collagen Rewet value as the difference between the wet and dry weight of the stack and record to the nearest 0.1 mg.

In like fashion, run a total of eight (8) replicates for each absorbent article to be evaluated. Calculate and report the Collagen Rewet (mg) for each dose as the arithmetic mean of the replicates to the nearest 0.1 mg.

4. Run-Off Test

Run-off is measured according to basic method for testing hydrophilic nonwovens in WSP 80.9 (05), standard test method for nonwoven run-off. The inclination angle is set to be 25°+/−1°. A total mass of test liquid of 25±0.5 g is used.

The topsheet sample is removed from the absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of the 100 mm×280 mm area. The specimen is carefully removed such that its longitudinal and lateral extension are maintained. A cryogenic spray (such as Cyto-Freeze, Control Company, Houston TX) can be used to remove the topsheet specimen from the underling layers, if necessary. The topsheet layer with 100 mm width is centered over the two 140 mm wide layers of reference filter paper.

If the dimensions of the absorbent article do not allow to excise an area of 100 mm×280 mm, then the largest possible rectangular topsheet area will be excised from the absorbent article with the procedure above. Multiple specimens will be removed from multiple absorbent articles and will be connected to each other with a 5 mm wide overlap on each neighboring side between two separate pieces. A double tape adhesive will be placed in the 5 mm wide overlap area, between the two layers being stitched together. This procedure will allow to create a 100 mm×280 mm area to be used according to basic method for testing hydrophilic nonwovens in WSP 80.9 procedure. For the testing, the tube, supplying the test liquid, will be placed between any overlap areas, in machine direction or cross direction.

EXAMPLES

Example 1: Nonwoven

Figure 13:
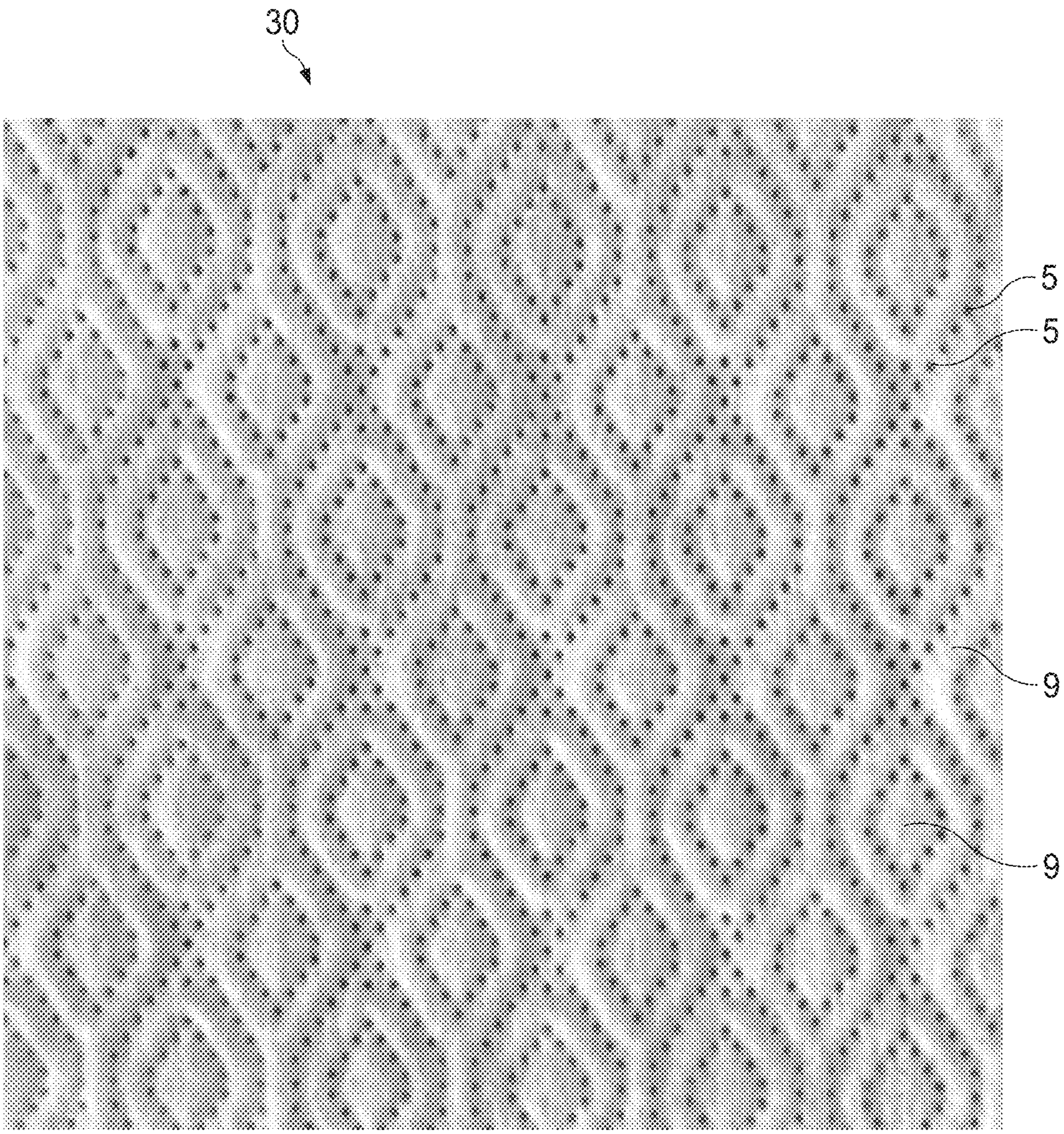
FIG. 13 is a schematic plan view of a nonwoven disclosed herein.

Nonwovens 1 and 2 were prepared using 24 gsm nonwoven made by 2.6D hydrophilic eccentric PE/PET bicomponent fibers as a first layer and 30 gsm carded air-through nonwoven made by 4D hydrophilic PE/PET fibers as a second layer. Nonwovens 3 and 4 were prepared using 24 gsm nonwoven made by 2.6D hydrophobic eccentric PE/PET bicomponent fibers as a first layer and 30 gsm carded air-through nonwoven made by 4D hydrophilic PE/PET fibers as a second layer. All nonwovens were apertured according to the pattern shown in FIG. 13. The nonwoven of FIG. 13 has apertures 5, land areas 8 and protrusions 9. Aperturing of Nonwoven 1 and Nonwoven 3 were carried out to coat apertures with a hydrophobic treatment and a hydrophilic treatment, respectively, simultaneously with formation of the apertures.

A contact angle ("first non-aperture area contact angle") of a non-aperture area in the first surface of the first layer and a contact angle ("aperture contact angle") of side walls of apertures in Nonwovens 1-3 prepared above were measured according to Contact Angle Test disclosed herein, and are shown in Table 2 below.

TABLE 2

| | Nonwoven 1 | Nonwoven 2 | Nonwoven 3 | Nonwoven 4 |
|---|---|---|---|---|
| 1st layer | 24 gsm hydrophilic nonwoven | Same as 1st layer of Nonwoven 1 | 24 gsm hydrophobic nonwoven | Same as 1st layer of Nonwoven 3 |
| 2nd layer | 30 gsm hydrophilic nonwoven | | | |
| Aperture coating material | Hydrophobic treatment | None | Hydrophilic treatment | None |
| first non-aperture area contact angle (°) | 54.41° ± 16.23° | 54.41° ± 16.23° | 93.45 ± 15.56 | Not tested |
| aperture contact angle (°) | 91.23 ± 7.0 | 69.5° ± 15.2° | 0 | Not tested |

Example 2. Absorbent Articles

Baby diapers 1-4 as exemplary absorbent articles having topsheets made by nonwovens in Example 1 above were fabricated using a common distribution layer, an absorbent core and a backsheet.

Acquisition speed, rewet, and run off each of Diapers 1-4 were measured according to Acquisition Speed Test, Rewet Test, and Run-off Test disclosed herein. Table 3 below includes the measurement results.

TABLE 3

| | | Diaper 1 | Diaper 2 | Diaper 3 | Diaper 4 |
|---|---|---|---|---|---|
| | Topsheet | Nonwoven 1 | Nonwoven 2 | Nonwoven 3 | Nonwoven 4 |
| Acquisition time (sec) | 25 ml | 81.7 | 82.8 | 92.3 | 88.8 |
| | 50 ml | 68.5 | 71.7 | 84.8 | 78 |
| | 75 ml | 127 | 149 | 181 | 181 |
| Rewet (mg) | | 0.0565 | 0.0945 | 0.059 | 0.0723 |
| Run-off (%) | 75 ml | 0 | 0 | Not tested | 11.8 |
| | 150 ml | 0 | 0 | Not tested | 0.0 |
| | 225 ml | 13 | 10.8 | Not tested | 15.5 |
| | 300 ml | 39.9 | 37.9 | Not tested | 36.9 |

Diaper 2 having a hydrophilic topsheet, compared to Diapers 3 and 4 with hydrophobic topsheets demonstrates an acquisition speed benefit but exhibits worse rewet as a hydrophilic topsheet allows better fluid distribution and penetration, and at the same time, allow more liquid to come back to surface of the topsheet both from absorbent core and from higher amount of retained liquid in the top sheet.

Diaper 1 having Nonwoven 1 as a topsheet exhibits a faster acquisition time and significantly lower rewet than Diaper 2 while it exhibits run-off parity to Diaper 2.

Diaper 1, compared to Diapers 3 and 4 with a hydrophobic topsheet, exhibits a significantly fast acquisition time, and significantly low rewet (compared to Diaper 4).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a wearer facing surface and a garment facing surface, the absorbent article comprising:
- a topsheet, a backsheet, and an absorbent core disposed between the topsheet and the backsheet;
- wherein the topsheet comprises a first layer free from cellulose-based fibers, the first layer comprising a first surface, an opposite second surface, and a plurality of apertures, wherein the first surface of the first layer forms at least part of the wearer facing surface;
- wherein the first surface of the first layer comprises a hydrophilic non-aperture area having a first non-aperture area contact angle as measured by Contact Angle Test; and
- wherein each of a majority of the plurality of the apertures has a side wall having an aperture contact angle as measured by Contact Angle Test, the aperture contact angle being higher than the first non-aperture area contact angle.

2. The absorbent article according to claim 1, wherein the difference between the first non-aperture area contact angle and the aperture contact angle is at least about 10°.

3. The absorbent article according to claim 1, wherein the aperture contact angle is equal to or higher than about 80° as measured by Contact Angle Test.

4. The absorbent article according to claim 1, wherein the non-aperture area comprises a hydrophilic treatment.

5. The absorbent article according to claim 1, wherein the side wall of the majority of the plurality of apertures is coated with a treatment with a HLB value not higher than about 13.

6. The absorbent article according to claim 1, wherein the apertures comprise pin apertures.

7. The absorbent article according to claim 1, wherein the topsheet comprise a second layer, and wherein the first layer partially interpenetrates the second layer in the apertures.

8. The absorbent article according to claim 7, wherein the second layer is not completely covered by the first layer in the apertures.

9. The absorbent article according to claim 1, wherein the first layer comprises a plurality of protrusions extending outwardly, away from a land area on the first surface.

10. The absorbent article according to claim 1, wherein the topsheet further a second layer, the second layer comprising a first surface, an opposing second surface and a plurality of apertures in such a way that the first surface of the second layer is in a face to face relationship with the second surface of the first layer.

11. The absorbent article according to claim 10, wherein the second layer comprises thermoplastic fibers.

12. The absorbent article according to claim 11, wherein the second surface of the second layer comprises a land area having a second non-aperture area contact angle, and wherein the second non-aperture area contact angle is not greater than the first non-aperture area contact angle.

13. The absorbent article according to claim 1, wherein first layer has at least 3% of open area.

14. A nonwoven comprising a first layer free from cellulose-based fibers, the first layer comprising a first surface, an opposite second surface, and a plurality of apertures;
- wherein the first surface of the first layer comprises a hydrophilic non-aperture area having a first non-aperture area contact angle as measured by Contact Angle Test; and
- wherein each of a majority of the plurality of the apertures has a side wall having an aperture contact angle as measured by Contact Angle Test, the aperture contact angle being higher than the first non-aperture area contact angle.

15. The nonwoven of claim 14, wherein the nonwoven comprises a second layer, the second layer comprising a first surface, an opposing second surface and a plurality of apertures, wherein the first surface of the second layer is in a face to face relationship with the second surface of the first layer.

16. The nonwoven of claim 15, wherein the second surface of the second layer has a land area having a second non-aperture area contact angle which is not greater than the first non-aperture area contact angle.

17. A method for producing an apertured nonwoven comprising steps of:
- a) providing a first layer free from cellulose-based fibers, a first surface and an opposite second surface;
- b) providing an aperturing apparatus comprising a first forming member and a second forming member which engages the first forming member, wherein the first forming member comprises a plurality of pins on its surface and the second forming member comprises a plurality of recesses on its surface;
- c) wetting the pins on the first forming member with a treatment having a HLB value not higher than about 13; and d) moving the first layer between the first and second forming members so that apertures are formed in the first layer as the pins on the first forming member and the recesses on the second forming member are engaged;

wherein the first surface of the first layer comprises a land area having a first non-aperture area contact angle measured by a Contact Angle Test; and wherein each of a majority of the plurality of the apertures has a side wall having an aperture contact angle as measured by the Contact Angle Test, the aperture contact angle being higher than the non-aperture area contact angle.

18. The method according to claim 17, wherein the step a) comprises providing a first layer comprising cellulose-based fibers, a first surface and an opposite second surface, and providing a second layer comprising a first surface and an opposite second surface in such a way that the first surface of the second layer is in a face to face relationship with the second surface of the first layer, and wherein step d) comprises moving the first layer and second layer between the first and second forming members in such a way that the first surface of the first layer faces the first forming member so that apertures are formed in the first layer and the second layer as the pins on the first forming member and the recesses on the second forming member are engaged.

* * * * *